United States Patent [19]
Sirhan

[11] Patent Number: 5,571,094
[45] Date of Patent: Nov. 5, 1996

[54] GUIDEWIRE REPLACEMENT DEVICE

[75] Inventor: Motasim M. Sirhan, Santa Clara, Calif.

[73] Assignee: Advanced Cardiovascular Systems, Inc., Santa Clara, Calif.

[21] Appl. No.: 168,571

[22] Filed: Dec. 16, 1993

Related U.S. Application Data

[63] Continuation of Ser. No. 818,288, Jan. 9, 1992, abandoned.

[51] Int. Cl.$^6$ .................................................. A61M 25/00
[52] U.S. Cl. ............................... 604/284; 606/1; 606/194
[58] Field of Search ................................. 606/192, 194, 606/1; 604/96, 284, 905

[56] References Cited

U.S. PATENT DOCUMENTS

| | | | |
|---|---|---|---|
| 2,624,341 | 1/1953 | Wallace | 604/284 |
| 3,835,863 | 9/1974 | Goldberg et al. | 604/284 |
| 4,142,528 | 3/1979 | Whelan et al. | 604/284 |
| 4,467,790 | 8/1984 | Schiff | 604/96 X |
| 4,569,347 | 2/1986 | Frisbie | 128/344 |
| 4,585,435 | 4/1986 | Vaillancourt | 604/284 X |
| 4,596,557 | 6/1986 | Pexa | 604/284 X |
| 4,616,652 | 10/1986 | Simpson | 128/344 |
| 4,661,110 | 4/1987 | Fortier et al. | 604/284 X |
| 4,748,982 | 6/1988 | Horzewski et al. | 128/344 |
| 4,915,704 | 4/1990 | Miyasaka et al. | 604/284 X |
| 4,932,413 | 6/1990 | Shockey et al. | 128/657 |
| 4,947,864 | 8/1990 | Shockey et al. | 128/772 |
| 4,988,356 | 1/1991 | Crittenden et al. | 604/96 X |
| 5,053,003 | 10/1991 | Dadson et al. | 604/284 X |
| 5,129,887 | 7/1992 | Euteneuer et al. | 604/96 X |
| 5,213,575 | 5/1993 | Scotti | 604/284 X |
| 5,281,203 | 1/1994 | Ressemann | 604/164 |

*Primary Examiner*—Michael H. Thaler
*Attorney, Agent, or Firm*—Crosby, Heafey, Roach & May

[57] ABSTRACT

A guidewire replacement device having an elongated catheter shaft with an inner lumen extending within the catheter shaft, a proximal guidewire port spaced at least 1 cm from the distal end of the catheter which is in fluid communication with the inner lumen and a distal guidewire port in the distal end of the catheter which is also in fluid communication with the inner lumen. The proximal end of an in-place guidewire is inserted through the distal guidewire port and advanced through the inner lumen until the proximal end of the guidewire extends through the proximal guidewire port. The exchange device is advanced over the guidewire until the distal end of the exchange device is seated within the proximal guidewire port in the readily exchangeable dilatation catheter. With the distal end of the exchange device well seated within the proximal guidewire port of the dilatation catheter, the in-place guidewire can be withdrawn from the patient. A replacement guidewire is advanced through the inner lumen of the exchange device until it exits the distal guidewire port of the exchange device into the inner guidewire receiving lumen of the dilatation catheter. Once the replacement guidewire is properly placed, the exchange device can then be withdrawn from the patient.

12 Claims, 5 Drawing Sheets

GUIDEWIRE REPLACEMENT DEVICE

This is a continuation of application Ser. No. 07/818,288 which was filed on Jan. 9, 1992, now abandoned.

BACKGROUND OF THE INVENTION

This invention generally relates to intravascular procedures, such as percutaneous transluminal coronary angioplasty (PTCA), and particularly to the exchange of guidewires during such procedures.

In classic PTCA procedures, a guiding catheter having a preshaped distal tip is percutaneously introduced into the cardiovascular system of a patient and advanced therein until the preshaped distal tip thereof is disposed within the aorta adjacent the ostium of the desired coronary artery. The guiding catheter is twisted or torqued from its proximal end, which extends outside of the patient, to turn the distal tip of the guiding catheter so that it can be guided into the coronary ostium and seated therein. A dilatation catheter having a dilatation balloon on the distal end thereof and a guidewire slidably disposed within an inner lumen of the dilatation catheter are introduced into and advanced through the proximal end of the guiding catheter to the distal tip of the guiding catheter seated within the coronary ostium. The distal tip of the guidewire is usually manually shaped (curved) by the physician or one of the attendants before it is introduced into the guiding catheter along with the dilatation catheter.

The shaped distal tip of the guidewire is first advanced out the distal tip of the guiding catheter into the patient's coronary artery. A torque is applied to the proximal end of the guidewire, which extends out of the proximal end of the guiding catheter as it is advanced within the coronary anatomy, to guide the curved or otherwise shaped distal end of the guidewire into a branch artery targeted for dilatation. The advancement of the guidewire within the target artery continues until it crosses the lesion to be dilated.

The dilatation catheter is then advanced out of the distal tip of the guiding catheter, over the previously advanced guidewire, until the balloon on the distal extremity of the dilatation catheter is properly positioned across the lesion to be dilated. Once properly positioned across the lesion, the flexible, relatively inelastic dilatation balloon on the catheter is inflated to a predetermined size with radiopaque liquid at relatively high pressures (e.g., generally 4–12 atmospheres) to dilate the stenosed region of the diseased artery. One or more inflations of the balloon may be required to complete the dilatation of the stenosis. After the last dilatation, the balloon is deflated so that the dilatation catheter can be removed from the dilated stenosis and so that blood flow can resume through the dilated artery.

Further details of guiding catheters, dilatation catheters, guidewires, and the like for angioplasty procedures can be found in U.S. Pat. No. 4,323,071 (Simpson-Robert); U.S. Pat. No. 4,439,185 (Lundquist); U.S. Pat. No. 4,468,224 (Enzmann et al. ); U.S. Pat. No. 4,516,972 (Samson); U.S. Pat. No. 4,438,622 (Samson et al.); U.S. Pat. No. 4,554,929 (Samson et al.); U.S. Pat. No. 4,582,185 (Samson); U.S. Pat. No. 4,616,652 (Simpson); U.S. Pat. No. 4,638,805 (Powell); U.S. Pat. No. 4,748,986 (Morrison et al.); U.S. Pat. No. 4,898,577 (Badger et al.); U.S. Pat. No. 4,748,982 (Horzewski et al.); and U.S. Pat. No. 4,821,722 (Miller et al.) which are hereby incorporated herein in their entirety by reference thereto.

The assignee of the present invention, Advanced Cardiovascular Systems, Inc., markets an improved dilatation catheter under the trademark ACS RX® Coronary Dilation Catheter which is described and claimed in U.S. Pat. No. 5,040,548 (Yock), U.S. Pat. No. 5,061,273 (Yock) and U.S. Pat. No. 4,748,982 (Horzewski et al.). This dilatation catheter has a short guidewire receiving sleeve or inner lumen extending through the distal portion of the catheter. The sleeve extends proximally a distance of at least 10 cm and usually not more than about 50 cm from a first guidewire port in the distal end of the catheter to a second guidewire port in the catheter spaced proximally from the inflatable balloon of the catheter. A slit is preferably provided in the catheter wall which extends distally from the second guidewire port, preferably to a location proximal to the proximal end of the inflatable balloon to aid in the removal of the catheter from a guidewire. The structure of the catheter allows for the rapid exchange of the catheter without the need for the use of an exchange wire or adding a guidewire extension to the proximal end of the guidewire. The design of this catheter has been widely praised by the medical profession and has met with much commercial success in the market place because of its unique design.

A substantial improvement in the rapid exchange type dilatation catheters, such as described above, has recently been made by McInnes et al. which is described in copending applications Ser. No. 07/476,056, filed Feb. 7, 1990 now abandoned and Ser. No. 07/541,264 filed Jun. 19, 1990, now abandoned both entitled READILY EXCHANGEABLE PERFUSION DILATATION CATHETER, which are incorporated herein by reference. In these readily exchangeable dilatation catheters, perfusion ports are provided in the catheter shaft proximal and distal to the balloon which are in fluid communication with the guidewire receiving inner lumen to allow blood to perfuse distal to the catheter when the balloon was inflated.

However, one inconvenience with the above described dilatation catheter systems adapted for rapid exchangeability has been the inability to remove a guidewire already in place within a patient's vasculature without losing access to the vascular location. There has been no convenient way in which a replacement guidewire might be advanced through the vasculature and into the short guidewire receiving inner lumen in the distal extremity of the dilatation catheter. The in-place guidewire may need to be replaced with another guidewire having a different structure, e.g. from a floppy-type design with a separate shaping ribbon to an intermediate or standard with a core wire which extends to the distal tip of the guidewire, or it may need to be withdrawn in order to reshape the distal tip and then be reinserted. In both instances the guidewire is referred to herein as the replacement guidewire.

What has been needed and heretofore unavailable is a intraluminal catheter system which provides for the easy and rapid exchange of both the catheter or the guidewire used to guide the catheter through a body lumen or both. The present invention satisfies these and other needs.

SUMMARY OF THE INVENTION

This invention is directed to a intraluminal catheter system which provides for the exchange of the guidewire and to the use of this system, particularly within the coronary arteries of a human patient during an angioplasty procedure.

The guidewire exchange device of the invention generally comprises an elongated catheter shaft with a guidewire receiving inner lumen extending therein to a guidewire port in the distal end of the catheter. A proximal guidewire port is provided in the catheter shaft spaced longitudinally at least 1 cm or more from the distal end of the shaft which is in fluid communication with the guidewire receiving inner lumen. The catheter shaft includes a relatively long proximal tubular section and a relatively short distal tubular section. The proximal guidewire port is located at or near the transition between the proximal and distal tubular sections of the exchange device. The distal tubular section is preferably adapted to guide the proximal end of a guidewire out the proximal guidewire port as the proximal end of the guidewire is advanced through the inner lumen of the guidewire exchange device from the distal guidewire port. In one preferred embodiment, the transition between the proximal and distal sections are slightly angled, e.g. about 5 to about 40 degrees, preferably about 5 to about 30 degrees, so that the proximal end of the guidewire will advance out the proximal guidewire port. The distal end of the distal tubular section of the guidewire exchange device is shaped, e.g. tapered, and dimensioned so as to be easily inserted into the proximal guidewire port of a readily exchangeable catheter as the exchange device is advanced over a guidewire which extends out the proximal guidewire port of the readily exchangeable catheter.

The guidewire exchange device is adapted to be advanced over a guidewire, which is disposed within a patient, either until the distal tip of the exchange device is seated within the proximal guidewire port of the readily exchangeable catheter or the distal end of the exchange device has been advanced through the guidewire port and well within the short guidewire receiving inner lumen which extends within the distal portion of the readily exchangeable catheter. Once the distal end of the guidewire exchange device is seated within the guidewire port, the in-place guidewire can then be withdrawn proximally from the catheter and the patient's arterial system by pulling on the proximal end of the guidewire which extends out of the patient. A replacement guidewire may then be advanced through the inner lumen of the exchange device, through the proximal guidewire port in the dilatation catheter and through the inner lumen of the catheter until the guidewire extends out the distal guidewire port in the dilatation catheter.

In the embodiment of the invention wherein the distal portion of the distal tubular member of the exchange device is adapted to be inserted into and be advanced through essentially the entire length of the relatively short guidewire receiving inner lumen of the readily exchangeable catheter is particularly suitable for use with a rapid exchange type dilatation catheters having perfusion ports, as described in the previously discussed McInnes et al. applications incorporated herein, which allow blood to pass through the guidewire receiving inner lumen. When using rapid exchange type dilatation catheters with perfusion holes in the catheter shaft, advancement of a replacement guidewire within the guidewire receiving inner lumen sometimes results in the passage of the guidewire out one of the perfusion holes in the catheter wall rather than the guidewire port in the distal end of the catheter. When the distal extremity of the guidewire exchange device of the invention is positioned within the guidewire receiving inner lumen of the readily exchangeable catheter, the replacement guidewire is directed to the distal guidewire port and cannot be advanced out one of the perfusion holes.

The construction of the junction between the distal and proximal sections can be used in a variety of intraluminal and intravascular devices including readily exchangeable dilatation catheters such as described in the aforementioned Yock and Horzewski et al. patents.

These and other advantages of the invention will become more apparent from the following detailed description thereof when taken in conjunction with the accompanying exemplary drawings.

DETAILED DESCRIPTION OF THE INVENTION

Figure 1:
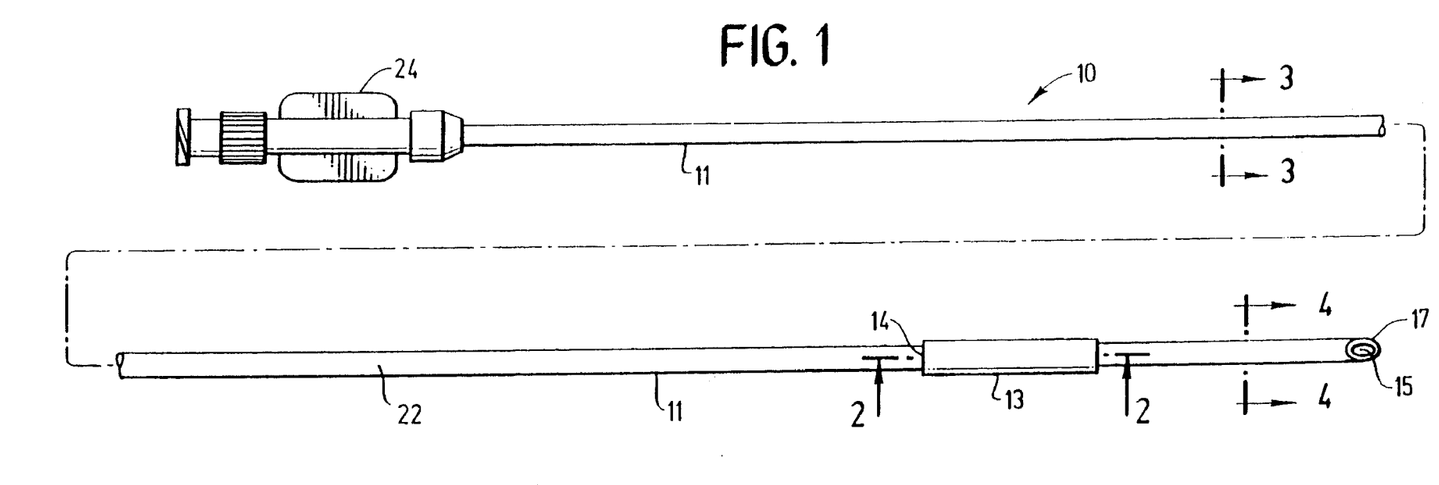
FIG. 1 is an elevational view of the exchange device of the invention.
Figure 2:
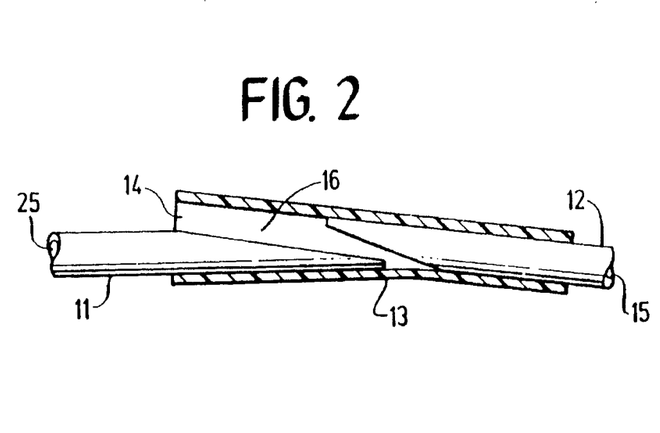
FIG. 2 is an enlarged elevational view in longitudinal section of the junction between the distal and proximal tubular members of the exchange device taken along the lines 2—2 shown in FIG. 1.

Reference is made to FIGS. 1–4 which depict a guidewire exchange device 10 embodying features of the invention. The exchange device 10 includes a relatively long proximal tubular section 11, a relatively short distal tubular section 12 and an outer sleeve 13 bonded at the junction between the proximal and distal tubular sections to the ends thereof. As shown in FIG. 2 the larger proximal end of the outer sleeve 13 defines a proximal guidewire port 14 communicating with the portion of the guidewire-receiving inner lumen 15 which extends within the distal tubular section 12 through a passageway 16. The distal tip 17 of the exchange device 10 may be beveled or tapered as shown to facilitate the entry thereof into the proximal guidewire port of a readily exchangeable catheter.

Figure 3:
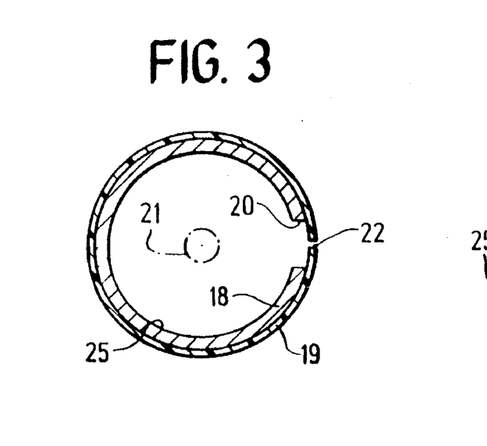
FIG. 3 is a transverse cross-sectional view taken along the lines 3—3 shown in FIG. 1.

The proximal tubular section 11 is relatively stiff in comparison to the distal tubular section 12 to provide a high degree of pushability to the catheter. As shown in FIG. 3, the proximal tubular section is formed of hypotubing 18 and a coating or jacket 19 of plastic material which is secured to the exterior of the hypotubing. The hypotubing is provided with a slit 20 having a width in excess of the maximum transverse dimension of the replacement guidewire 21 (shown in phantom) to be used and the jacket with a slit 22 having a much smaller spacing. This allows the replacement guidewire 21 to be stripped from the inner lumen 23 of the proximal section 11 after it has been advanced into the distal section 12. Preferably, a Luer adapter 24 is mounted to the proximal end of the proximal tubular section 11 and is either removable or is provided a slit continuous with slits 20 and 22 to facilitate removal of the replacement guidewire 21 from the inner lumen 25 in the proximal tubular section 11.

Figure 4:
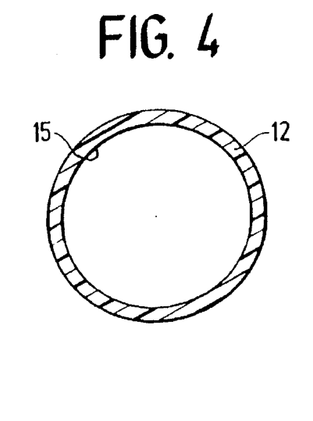
FIG. 4 is a transverse cross-sectional view taken along the lines 4—4 shown in FIG. 1.

FIG. 4 illustrates a transverse cross-sectional view of the proximal tubular section 12 which is a relative flexible section formed of suitable plastic material.

Figure 5:
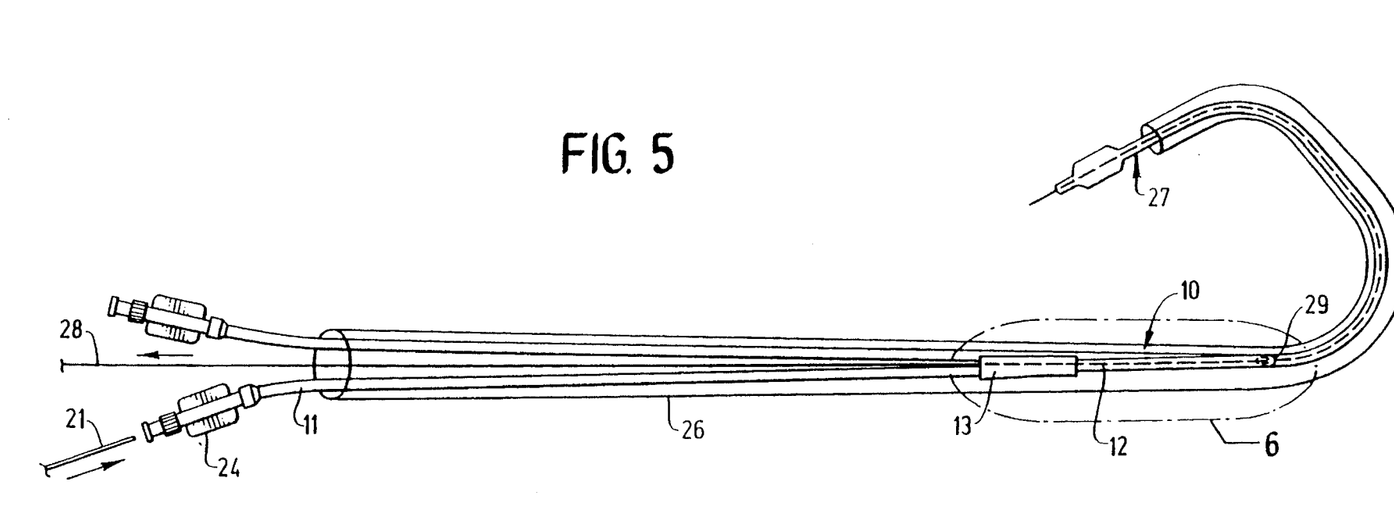
FIG. 5. is an elevational view of a guiding catheter and a readily exchangeable dilatation catheter with a guidewire exchange device having features of the invention.

FIG. 5 depicts a dilatation catheter assembly which includes a guiding catheter 26, a readily exchangeable dilatation catheter 27, an in-place guidewire 28, a replacement guidewire 21 and the guidewire exchange device 10. In practice, an adapter (not shown) would be provided on the proximal end of the guiding catheter which has a hemostatic valve large enough to accommodate the guidewire, the dilatation catheter and the exchange device.

Figure 6:
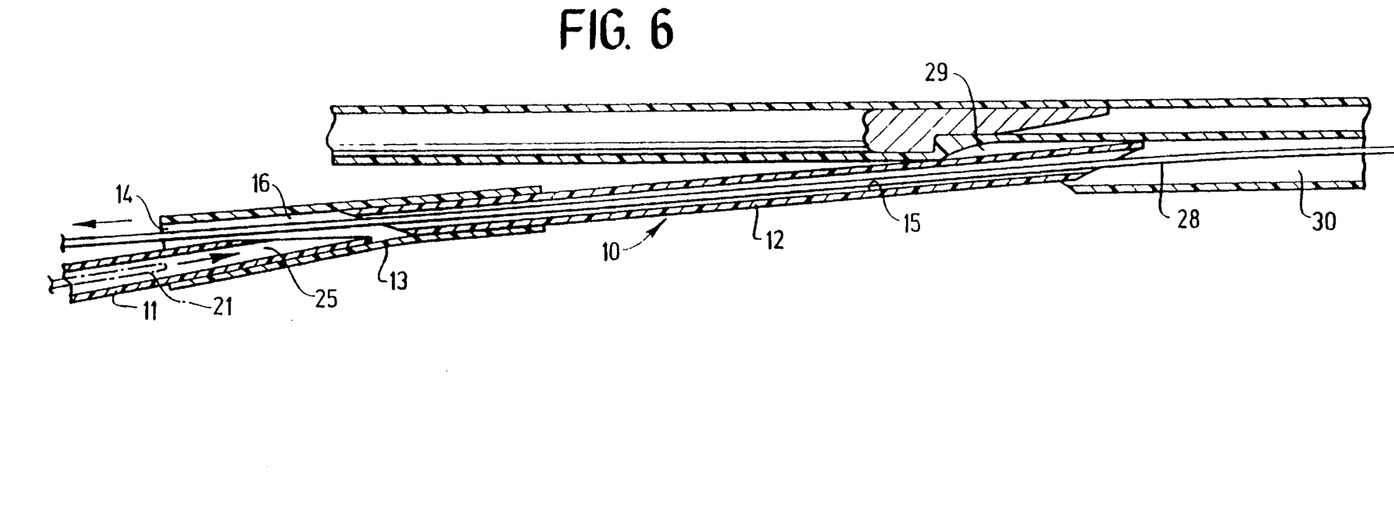
FIG. 6 is an enlarged view of the section of the assembly shown in FIG. 5 which is encircled by the ellipse 6.

The area enclosed by the ellipse 6 shown in FIG. 5 is depicted in an enlarged cross-sectional view in FIG. 6. The distal tip of the exchange device 10 is shown seated within the proximal guidewire port 29 of the dilatation catheter 27. A first guidewire 28 is in-place within the guidewire receiving inner lumen 30 of the dilatation catheter 27 and extends through the inner lumen 15 of the guidewire exchange device 10, the passageway 16 and the proximal port 14. The sleeve 13 is preferably enlarged at its proximal extremity and slightly angled as shown, e.g. about 5 to about 40 degrees, preferably about 5 to about 30 degrees, so that the guidewire passes straight through the passageway 16 and proximal port 14 when the guidewire is advanced proximally through the inner lumen 15 in the distal section 12. There is little or no tendency for the guidewire to advance into the inner lumen 25. A second or replacement guidewire 21 is shown in phantom disposed within the inner lumen 25 within the proximal tubular section 11.

Figure 7:
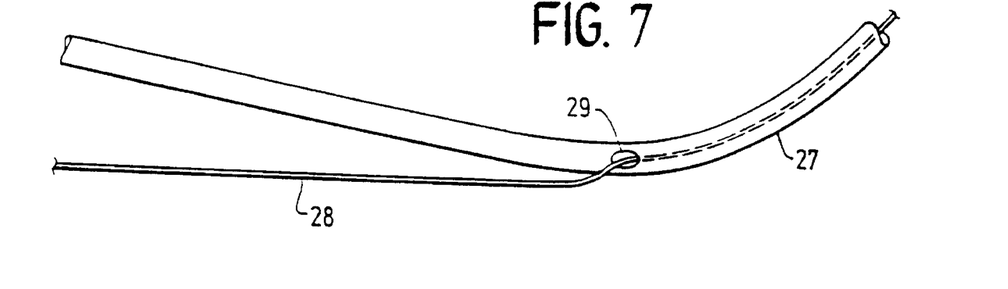
FIGS. 7–14 illustrate the exchange of a guidewire utilizing the exchange device shown in FIGS. 1–4.

The exchange of an in-place guidewire 28 with a replacement guidewire 21 is illustrated in the sequence of FIGS. 7–14. As shown in FIG. 7, the in-place guidewire is disposed within the short guidewire receiving inner lumen 30 (not shown) in the distal section of the readily exchangeable dilatation catheter 27. Both the in-place guidewire 28 and the dilatation catheter 27 are disposed within a guiding catheter 26, as shown in FIG. 5 with the distal end of the dilatation catheter extending out the distal end of the guiding catheter. As discussed in the Background of the Invention, the distal end of the guiding catheter 26 is seated within the ostium of the patient's coronary artery during the angioplasty procedure so as to guide the guidewires and dilatation catheters into the patient's coronary anatomy.

Figure 8:
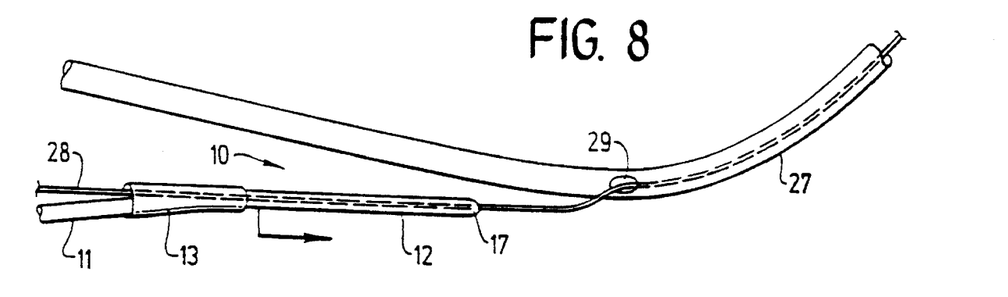
Figure 9:
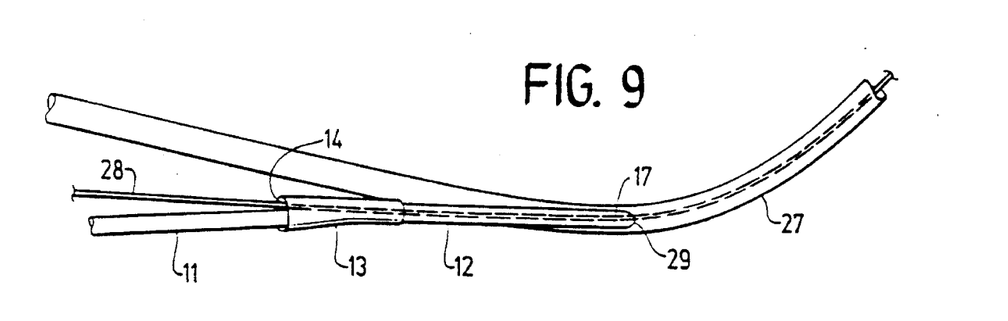
Figure 10:
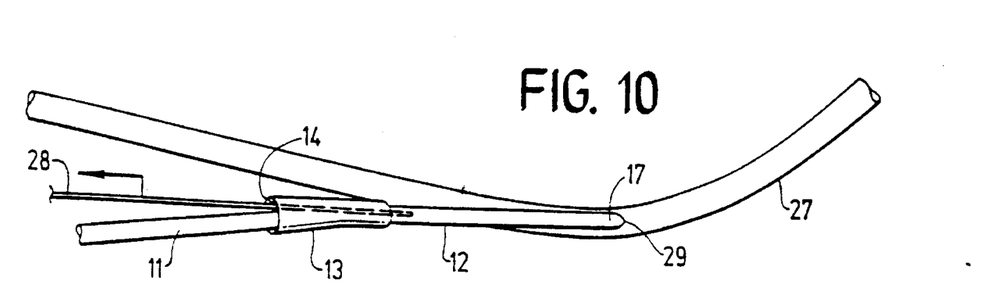
Figure 11:
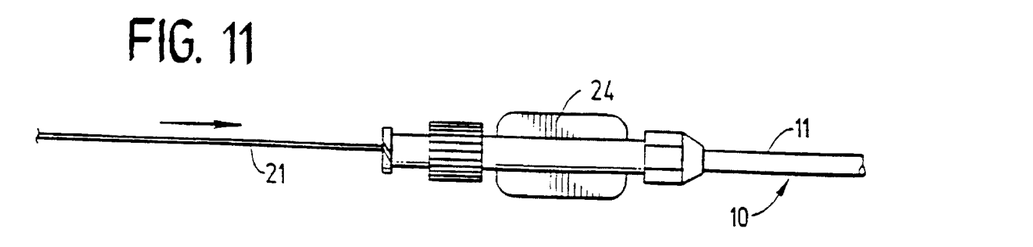
Figure 12:
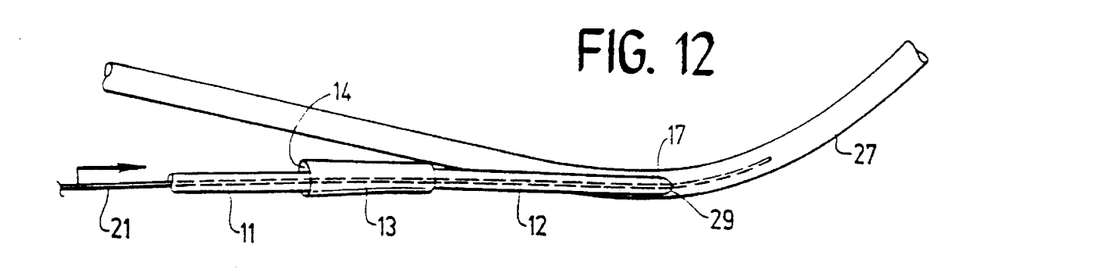
Figure 13:
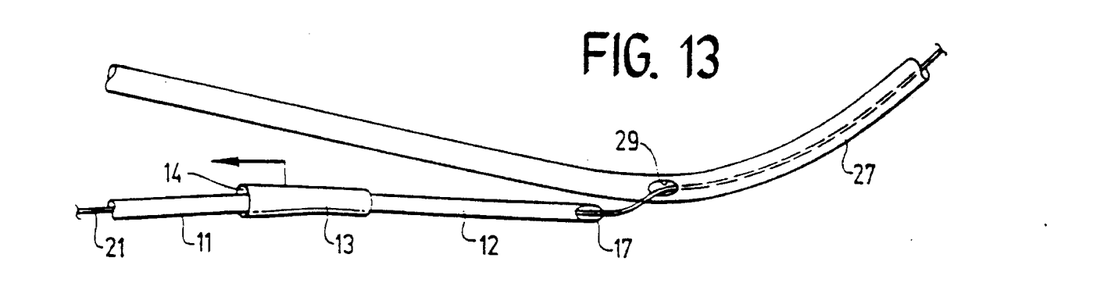
Figure 14:
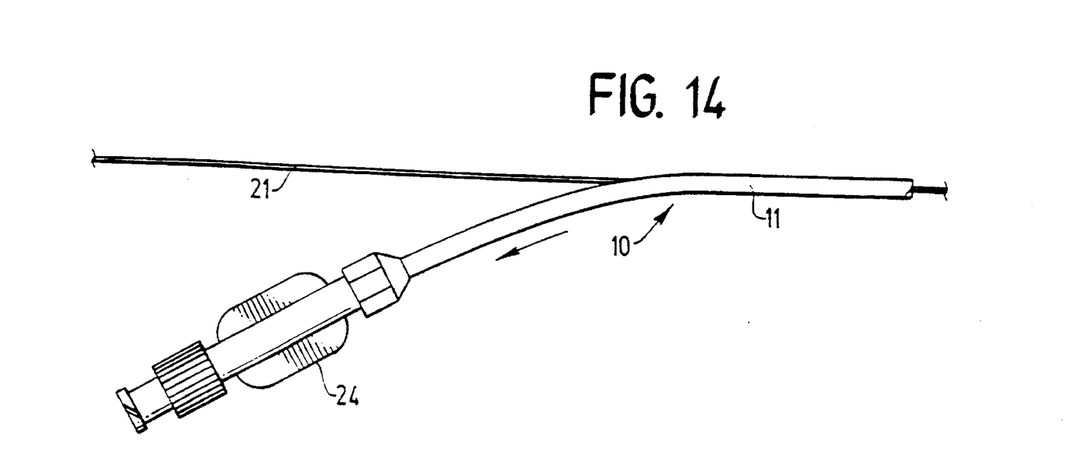

The proximal end of the in-place guidewire is inserted, i.e. back-loaded, into the distal port of the guidewire exchange device 10 and through the inner lumen 15 and passageway 16 until the proximal end exits the proximal port 14 at the junction between the proximal and distal tubular sections 11 and 12. The proximal end of the guidewire may then be manually grasped and the exchange device 10 advanced, as shown in FIG. 8, over the in-place guidewire 28 until the distal tip of the exchange device is seated within the proximal guidewire port 29 in the readily exchangeable dilatation catheter 27, as shown in FIG. 9. At this point the in-place guidewire 28 may be withdrawn from the dilatation catheter 27 and the patient as shown by the arrow in FIG. 10. The distal end of a replacement guidewire 21 is advanced through the adapter 24 as shown in FIG. 11 and the inner lumens 15 and 25 of the exchange device 10 and out the tapered distal end 17 thereof which is seated within the guidewire port 29 of the easily exchangeable dilatation catheter 27. As shown in FIG. 5 the replacement guidewire 21 may be positioned within the inner lumen 25 before the in-place guidewire 28 is removed. The advancement of the replacement guidewire 21 continues until the distal tip thereof extends out the distal end of the dilatation catheter 27 into the patient's coronary artery. The exchange device may then be removed from the patient. As the guidewire exchange device is withdrawn from the patient, it is stripped from the replacement guidewire 21 through slits 20 and 21 in the proximal section 11 as shown in FIG. 14. When the guidewire exchange device is withdrawn completely from the patient so that the replacement guidewire 21 extends out the proximal port 14 and bare guidewire 21 is visible extending out the distal end 17 of the exchange device, the exposed guidewire distal to the distal end 17 can be manually grasped to hold the guidewire in position while the exchange device is removed therefrom.

The readily exchangeable dilatation catheter 27 can be exchanged for another readily exchangeable dilatation catheter over either the in-place guidewire 28 or the replacement guidewire 21.

Figure 15:
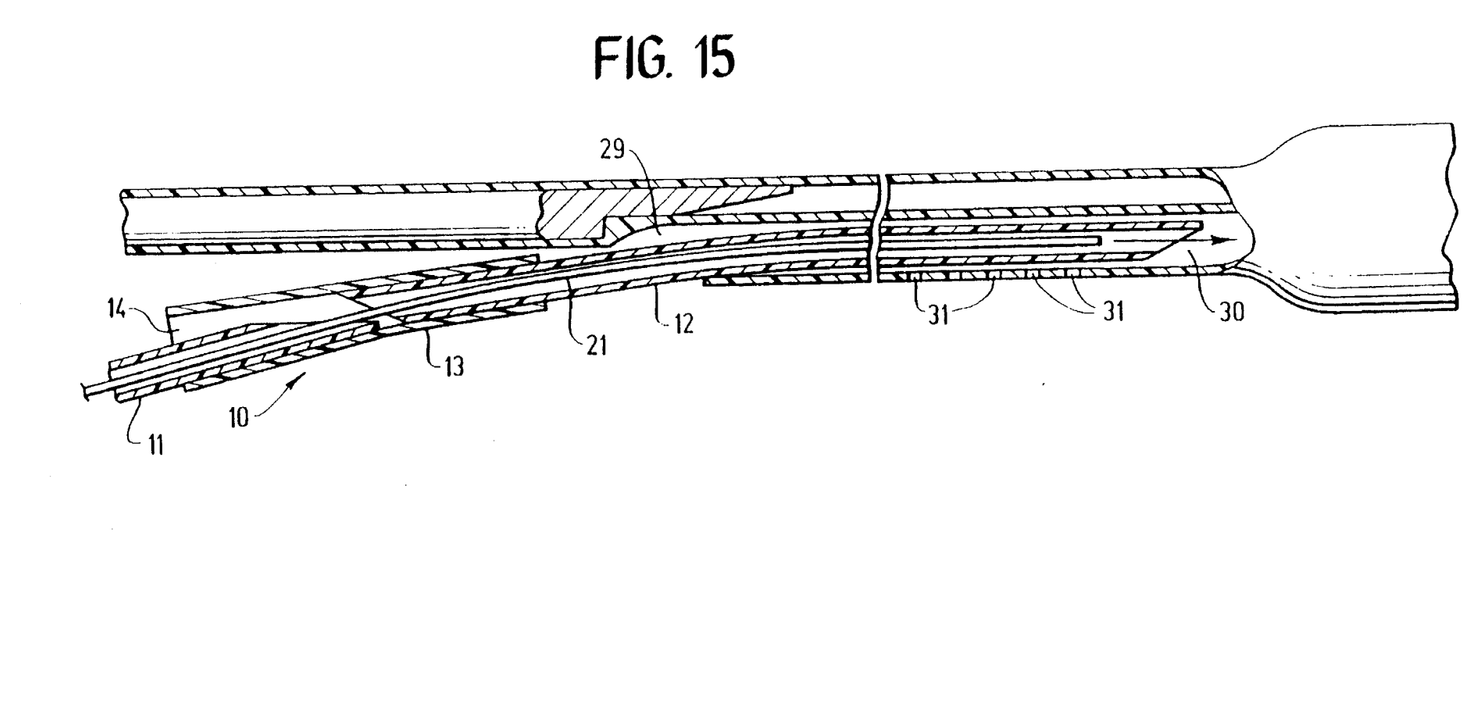
FIG. 15 is an enlarged longitudinal cross-sectional view similar to FIG. 6 of an alternate embodiment of the invention used with a dilatation catheter which has the capability of perfusing blood distal to the catheter upon the inflation of the balloon.

The procedure for a readily exchangeable dilatation catheter with perfusion ports proximal and distal to the inflatable member or balloon on the distal portion of the catheter is essentially the same as illustrated in FIGS. 7–14 except that the distal section 12 of the guidewire exchange device 10 extends well into the inner lumen 30 as shown in FIG. 15 to ensure that the guidewire does not divert out one of the perfusion ports 31 when the guidewire is advanced through the inner lumen 30.

The overall length of the guidewire exchange device is typically about 85 to about 130 cm. The transverse dimensions are for the most part controlled by the maximum transverse dimension of the guidewires to be used but they generally range from about 0.03 to about 0.05 inch (0.76–1.3)mm outer diameter. The length of the distal section can ranged from about 1 to about 40 cm, but preferably ranges from about 7 to about 20 cm. The hypotubing of the proximal section 11 can be formed of stainless steel or a superelastic NiTi alloy and the jacket can be a low density polyethylene. The distal section 12 and the sleeve 13 may be formed of a high density polyethylene. The guiding catheter, the dilatation catheter and the guidewires can be of conventional construction and materials.

While the invention has been described herein in terms of a catheter device which facilitates guidewire replacement in a readily exchangeable dilatation catheter, improved catheter construction can be employed in dilatation catheters such a readily exchangeable dilatation catheters. Those skilled in the art will recognize that other modifications and improvements can be made to the invention without departing from the scope thereof.

What is claimed:

1. An intravascular guidewire exchange device comprising,
    an elongated shaft which has a length of at least about 85 cm and which is configured for percutaneous introduction into and advancement within a human patient's vasculature to the coronary artery thereof, said shaft including:
        a flexible distal shaft section which has at least a distal portion thereof configured to be advanced through the patient's coronary artery and into a proximal guidewire port of a rapid exchange type intravascular catheter, proximal and distal ends, a first guidewire port in the distal end and a second guidewire port in the proximal end, a first open guidewire receiving inner lumen extending therein from the first guidewire port in the distal end thereof to the second guidewire port spaced proximally from the distal guidewire port and a longitudinally extending axis;
        a proximal shaft section having a length much greater than the distal shaft section,
a proximal end,
a distal end which is secured to the distal shaft section at a location between the first and second guidewire ports,
a third guidewire port in the distal end of the proximal shaft section which is located proximal to the first guidewire port and distal to the second guidewire port and which is in fluid communication with the first guidewire lumen,
a fourth guidewire port in the proximal end of the proximal shaft section
a second open guidewire receiving inner lumen which is disposed within the proximal shaft portion, which extends between the third and fourth guidewire ports in the proximal shaft portion and intercommunicates with the first guidewire receiving inner lumen in the distal shaft portion through the third guidewire port in the distal end of the proximal shaft portion and which has a longitudinal axis extending therein; and
the longitudinal axis of the second guidewire receiving inner lumen intersecting with the longitudinal axis of the first guidewire receiving inner lumen at an acute angle.

2. The guidewire exchange device of claim 1 wherein the second guidewire port in the distal shaft section is spaced proximally a least about 1 cm from the first guidewire port of the distal shaft section.

3. The guidewire exchange assembly of claim 1 wherein the second guidewire port in the distal shaft section is spaced proximally a least about 1 cm from the first guidewire port of the distal shaft section.

4. The intravascular guidewire exchange device of claim 1 wherein a distal portion of the proximal shaft section is oriented at an angle with respect to a proximal portion of the distal shaft section.

5. The intravascular guidewire exchange device of claim 1 wherein a distal portion of the proximal shaft section is off-set with respect to a proximal portion of the distal shaft section.

6. An intravascular guidewire exchange assembly comprising,
a) an intravascular exchange device having an elongated shaft which has a length of at least about 85 cm, which is configured for percutaneous introduction into and advancement within a human patient's vasculature to a coronary artery thereof and which includes:
a flexible distal shaft section which has at least a distal portion thereof configured to be advanced through the patient's coronary artery and into a proximal guidewire port in a rapid exchange type intravascular catheter disposed within the patient's coronary artery, proximal and distal ends, first guidewire port configured to slidably receive a guidewire in the distal end and a second guidewire port configured to slidably receive a guidewire in the proximal end, a first open guidewire receiving inner lumen extending therein from the first guidewire port in the distal end thereof to the second guidewire port spaced proximally from the distal guidewire port and having a longitudinal axis extending therein; and
a proximal shaft section which has a length much greater than the distal shaft section, a proximal end, a distal end which is secured to the distal shaft section at a location proximal to the first guidewire port and distal to the second guidewire port in the distal shaft section, a third guidewire port configured to slidably receive a guidewire in the distal end of the proximal shaft section located distal to the second guidewire port and proximal to the first guidewire port, a fourth guidewire port configured to slidably receive a guidewire in the proximal end of the proximal shaft section and a second open guidewire receiving inner lumen disposed within the proximal shaft portion extending between the third and fourth guidewire ports in the proximal shaft portion, intercommunicating with the first guidewire receiving inner lumen in the distal shaft portion through the third guidewire port in the distal end of the proximal shaft portion, and having a longitudinal axis which intersects the longitudinal axis of the first guidewire receiving inner lumen at an acute angle; and
b) a guidewire slidably disposed within one of the guidewire receiving inner lumens within the proximal shaft section or the distal shaft section.

7. The intravascular guidewire exchange assembly of claim 6 wherein a distal portion of the proximal shaft section of the intravascular exchange device is oriented at an angle with respect to a proximal portion of the distal shaft section.

8. The intravascular guidewire exchange assembly of claim 6 wherein a distal portion of the proximal shaft section of the intravascular exchange device is off-set with respect to a proximal portion of the distal shaft section.

9. An intravascular assembly comprising:
a) a rapid exchange type intravascular catheter having an elongated shaft which is configured for percutaneous introduction into and advancement within a human patient's vasculature to a coronary artery thereof, said shaft including
a flexible distal shaft section which has at least a distal portion thereof configured to be advanced through the patient's coronary artery, a first guidewire port in the distal end of the catheter shaft and a second guidewire port in the catheter shaft spaced proximal from the distal end of the catheter shaft, a guidewire receiving inner lumen extending within the distal portion of the catheter shaft from the first guidewire port in the distal end thereof to the second guidewire port; and
b) a guidewire exchange device having an elongated shaft which has a length of at least about 85 cm and which is configured for percutaneous introduction into and advancement within a human patient's vasculature to a coronary artery thereof, said shaft including
a flexible distal shaft section which has at least a distal portion thereof configured to be advanced through the patient's coronary artery and disposed within the second guidewire port in the rapid exchange type intravascular catheter, proximal and distal ends, a first guidewire port in the distal end configured to slidably receive a guidewire and a second guidewire port in the proximal end configured to slidably receive a guidewire, a first open guidewire receiving inner lumen extending therein from the first guidewire port in the distal end thereof to the second guidewire port spaced proximally from the distal guidewire port and having a longitudinal axis extending therein, and
a proximal shaft section which has a length much greater than the distal shaft section, a proximal end, a distal end which is secured to the distal shaft section at a location proximal to the first guidewire port and distal to the second guidewire port, a third guidewire port configured to slidably receive a guidewire in the distal end of the proximal shaft section, a fourth guidewire port configured to slidably receive a guidewire in the proximal end of the proximal shaft section and a second open guidewire receiving inner lumen disposed within the proximal shaft portion and extending between the third and fourth guidewire ports in the proximal shaft portion, intercommunicating with the first guidewire receiving inner lumen in the distal shaft portion through the third guidewire port in the distal end of the proximal shaft portion, and having a longitudinal axis which intersects with the longitudinal axis of the first guidewire receiving inner lumen at an acute angle.

10. The intravascular assembly of claim 9 including a guidewire slidably disposed at least within the second guidewire receiving inner lumen within the proximal shaft section of the guidewire exchange device.

11. The intravascular assembly of claim 9 wherein a distal portion of the proximal shaft section of the guidewire exchange device is oriented at an angle with respect to a proximal portion of the distal shaft section.

12. The intravascular assembly of claim 9 wherein a distal portion of the proximal shaft section of the guidewire exchange device is off-set with respect to a proximal portion of the distal shaft section.

* * * * *